United States Patent
Foedisch et al.

(10) Patent No.: US 6,752,003 B2
(45) Date of Patent: Jun. 22, 2004

(54) METHOD AND DEVICE FOR THE EXTRACTIVE TRIBOELECTRIC MEASUREMENTS OF DUST AND AEROSOLS IN STREAMING GASES

(75) Inventors: Holger Foedisch, Leipzig (DE); Petra Schengber, Merseburg (DE); Michael Ulbrich, Leipzig (DE)

(73) Assignee: Dr. Foedisch Umweltmesstechnik GmbH, Markranstadt OT Kulkwitz (DE)

( * ) Notice: Subject to any disclaimer, the term of this patent is extended or adjusted under 35 U.S.C. 154(b) by 0 days.

(21) Appl. No.: 10/275,138

(22) PCT Filed: May 1, 2001

(86) PCT No.: PCT/DE01/01674
§ 371 (c)(1),
(2), (4) Date: Dec. 26, 2002

(87) PCT Pub. No.: WO01/84116
PCT Pub. Date: Nov. 8, 2001

(65) Prior Publication Data
US 2003/0110829 A1 Jun. 19, 2003

(30) Foreign Application Priority Data
May 2, 2000 (DE) .......................................... 100 22 391
Apr. 30, 2001 (DE) .......................................... 101 21 620

(51) Int. Cl.⁷ ............................................. G01N 37/00
(52) U.S. Cl. ................................................... 73/28.02
(58) Field of Search ........................... 73/865.5, 28.02, 73/23.2, 28.5; 356/37; 324/71.4, 464

(56) References Cited

U.S. PATENT DOCUMENTS

| | | | |
|---|---|---|---|
| 2,307,602 A | * | 1/1943 | Penney et al. ............. 73/28.01 |
| 2,857,978 A | * | 10/1958 | Lenger .......................... 183/7 |
| 3,178,930 A | * | 4/1965 | Moore et al. ............... 73/28.01 |
| 3,444,667 A | * | 5/1969 | Mullin ......................... 55/113 |
| 3,679,973 A | * | 7/1972 | Smith, Jr. et al. .......... 324/71 R |
| 3,718,029 A | * | 2/1973 | Gourdine et al. ........... 73/28.01 |
| 3,794,909 A | | 2/1974 | Smith .......................... 324/32 |
| 3,827,217 A | * | 8/1974 | Volsy .......................... 55/121 |
| 4,140,005 A | | 2/1979 | Kittelson ....................... 73/28 |
| 4,179,934 A | | 12/1979 | Svarovsky .............. 73/432 PS |
| 4,531,402 A | * | 7/1985 | Reif et al. ...................... 73/28 |
| 5,532,599 A | * | 7/1996 | Stearns et al. ............... 324/464 |
| 5,892,364 A | * | 4/1999 | Monagle ..................... 324/464 |
| 6,018,985 A | * | 2/2000 | Lane-Smith ................ 73/28.02 |
| 6,454,862 B1 | * | 9/2002 | Yoshida et al. ............. 118/722 |
| 6,568,245 B2 | * | 5/2003 | Kaufman .................... 73/28.02 |

FOREIGN PATENT DOCUMENTS

| | | |
|---|---|---|
| DE | 297 902 | 1/1992 |
| DE | 197 29 144 | 2/1999 |
| DE | WO 99 41585 | 8/1999 |

* cited by examiner

Primary Examiner—Hezron Williams
Assistant Examiner—Charles D. Garber
(74) Attorney, Agent, or Firm—Jordan and Hamburg LLP

(57) ABSTRACT

A method and a device for the extractive triboelecric measurement of dust and aerosols is provided. A partial gas stream is removed from a main stream and drawn through a triboelecric measuring chamber with a variable or constant temperature, at a variable or constant speed and with an abradant rotational movement. Sensors are arranged in the measuring chamber in such a way that they are electrically insulated. The triboelecric effect begins when the gas stream that is loaded with dust particles and aerosols passes through the triboelecric measuring chamber, preferably in a cyclonic manner, moving rotationally, abradantly on the sensors. Since gaseous components cannot be measured according to the triboelecric measuring principal, the temperature is controlled intermittently at a low temperature producing a signal which is caused by dust and aerosols, and at a higher temperature, producing a signal which is caused by dust alone.

26 Claims, 11 Drawing Sheets

FIG-8    Cross Section A-A

Cross Section B-B

FIG-9

FIG-10  Cross Section C-C

METHOD AND DEVICE FOR THE EXTRACTIVE TRIBOELECTRIC MEASUREMENTS OF DUST AND AEROSOLS IN STREAMING GASES

BACKGROUND

The invention relates to a method and a device for measuring dust and aerosols in streaming gases using the triboelectrical principle, with its signaling effect being amplified by taking appropriate measures as regards process-engineering and hardware design.

To use the invention, a partial stream is branched off from the main stream and conditioned in a way deemed fit for the purpose, after which the dust and aerosol content is determined by making use of the triboelectrical principle.

In their technical paper "Grundlage Ladungsdifferenz, triboelektrische Staubmessung unter theoretischen and praktischen Gesichtspunkten" 1, published as reprint from "Verfahrenstechnik" 12/97, H Fodisch and D Richter suggest—among other things—that charge transfer occurs when two bodies are brought in contact to each other by touching or rubbing. The surface atoms exchange their electrons so that a boundary layer is created with a positive and a negative surface charge being very close to each other, in a molecular scale. The differential charge forms the basis of triboelectric measuring devices. Among other things, the impact of the dust particles' velocity on the measuring result is discussed in the above paper, and the findings suggest that after calibration the dust concentration can be determined by combining triboelectric signal and velocity for a certain measurement problem.

A novel dust measuring device, based on the triboelectrical principle, was introduced by H Fodisch, P Schengber and U Riemann, as published in "VDI Berichte", N 1443, 1999, p. 447–458. To this end, reference is also made to the publication of the unexamined application DE 197 29 144 A1, according to which highly precise measuring results are obtained due to the selected probe design in connection with an appropriate scoring hardware. The related dust concentration measuring device is employed for continuous dust content measurements, in particular for pollution control and determination of dust concentration in process monitoring applications. Also, it should be underlined that above all the impact of the dust particles' velocity on the triboelectric signal was evaluated in an appropriate way so that reproducible results could be obtained.

Furthermore, reference is made to the printed patent specification DD 297 902 A7. The invention is based on the problem of automatically sampling a partial stream from a solid matter laden gas main stream, allowing identical dispersion conditions in both the gas main and partial stream in view of the measuring process to follow.

The reason why reference is made to the printed patent specification DD 297 902 A7 is because also in this invention, to be described in greater detail herein below, a gas stream is branched off and measurements taken after the stream is treated in an appropriate way. To all intents and purposes, sampling a partial stream is an extractive dust measuring method.

Taking into account the prior art, this is to suggest a method and a device for measuring dust and aerosols by which, after sampling a partial stream, the triboelectric effect is used with the object of obtaining a higher signal quality and an improved method for scoring the measurements.

SUMMARY

According to the invention the problem is solved as described herein below.

The solution to the problem is now described in further detail. As already mentioned, rubbing two bodies against each other will create a positive and a negative charge, with the difference between these two charges being the fundamental effect triboelectric measuring devices are relying on. The level of the potential difference, that is to say the amount of charge exchanged, depends on a great number of factors. One dependence results from the materials' electric properties. The much more decisive factors, however, are of a mechanical nature, such as the streaming particles' velocity, the duration of contact, the size of exchange area, the rubbing intensity and the frequency of contacts. Therefore, the inventive proposal, forming the basis of a new generation of triboelectric measuring devices, works on the assumption that it should be possible to adjust stream conditions and flue gas boundary parameters is such a way as is suited for determining dust content, aerosols concentration and/or dust and aerosols together in the stream branched off. This will be achieved by specifically varying the partial gas stream's temperature in such a way that aerosols alternatively evaporate or exist in form of liquid drops that can be measured by using the triboelectric effect. As regards the technical implementation, the partial gas stream is heated and—if required—diluted to a definite mixture by adding dry, pre-heated, dust-free air.

In this invention, the intensity with which dust and aerosol particles are rubbing across the sensors, that may come in different shape and surface types, is increased by some kind of particle cycloning when they are moving through the triboelectrical measuring chamber.

In contrast to in-situ measurements, in which the gas main stream may have diameters of several meters which in turn makes it difficult to control its flow rate, it now becomes possible to maintain constant conditions as regards the partial stream branched-off and considerably increase its velocity when entering the measuring chamber. Due to the stream's cyclonic motion, a large distance is covered inside the measuring chamber. Hence, both duration and intensity of rubbing as well as frequency of contacts can be directly controlled and changed if needed.

The triboelectrical measuring chamber may be arranged immediately inside as well as outside the gas main stream. In all cases, the signal recording will be effected by one or more measuring probes, all of them being subjected to the same flowing conditions inside the triboelectrical measuring chambers.

The measuring probes' design include separately arranged shells or other probes with definite flow resistance values which will be further discussed herein below.

Also, horizontal or vertical flow conditions at probes situated in central locations or other places are possible, after having increased the dust and aerosol particles' velocity in advance.

The triboelectric signals are conducted by appropriate electric cables and transmitted to further processing.

The probe for sampling the dust-laden gas and/or dust-and-aerosol particle mixture can be heated and is designed in such a way that right after the partial gas stream (at a temperature similar to that of the gas main stream) enters the sampling probe a diluent air stream at a definite temperature can be added to the partial gas stream by using a proportioning nozzle. The partial gas stream, after possible dilution now being the measuring gas stream, is accelerated by means of an injector and guided through the triboelectrical measuring chamber.

Using for example a multi-way spherical valve, both triboelectrical measuring chamber and sampling probe can be flushed with flushing air.

A volume flow metering and/or monitoring device is integrated in the gas metering section so that constant conditions can be maintained for the partial gas stream, or computerized compensation is enabled as regards the impact the volume flow fluctuations may have on the triboelectric signal, respectively.

BRIEF DESCRIPTION OF THE DRAWINGS

Below, the invention will be described by a practical example. The figures show pictorial schematics as follows.

DETAILED DESCRIPTION

Figure 1:
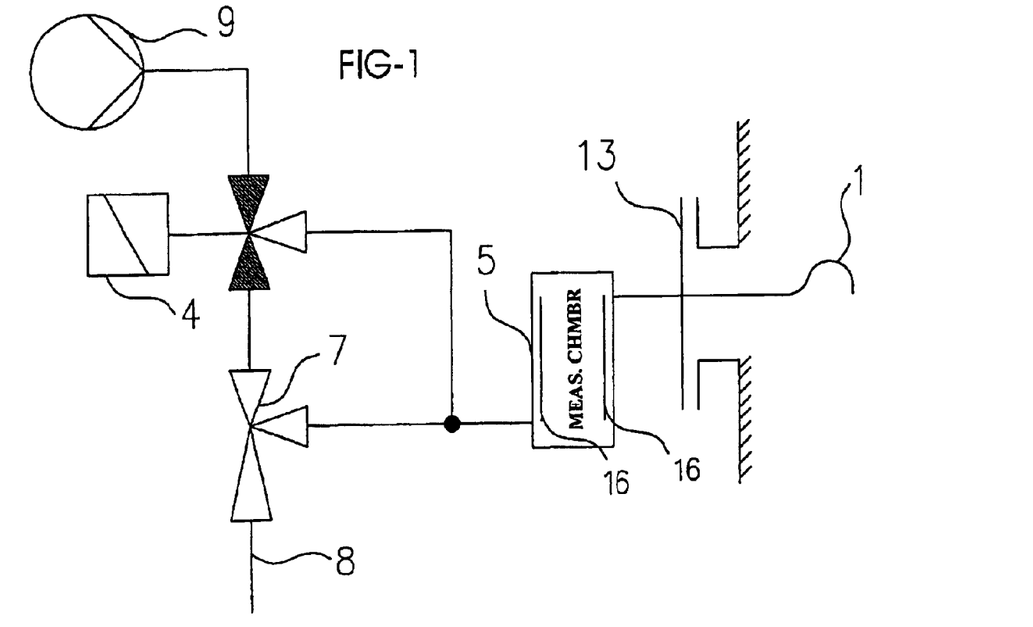
FIG. 1—Device for continuous extractive dust content measurements with the measuring chamber being arranged outside the gas main stream FIG. 2—Device for continuous extractive dust content measurements with tree measuring chamber being arranged inside the gas main stream FIG. 3—Device for continuous extractive dust content measurements in moist and tacky flue gases FIG. 4—Aerosol measurements by means of a device for continuous extractive dust content measurements using a specific chamber with an intermittent temperature regime FIG. 5—Device for aerosol measurements, using two parallel triboelectrical measuring chambers working at two different temperature levels FIG. 6—Longitudinal section view of a triboelectrical, tube-shaped measuring chamber with some kind of a forced cycloning of gas particles FIG. 7—Longitudinal sectional view of a triboelectrical, tube-shaped measuring chamber according to FIG. 6, where the distance between two shell-like sensors can be distinguished FIG. 8—Sectional view A—A, according to FIG. 6

As shown in FIG. 1, a hook-shaped probe (1) the diameter of which is designed for an isokinetic sampling projects into the into the gas main stream flowing through a flue duct. A flange (13) is used to secure the hook-shaped probe (1) onto the flue duct. The probe for sampling measuring gas (2) is arranged downstream the hook-shaped probe (1). Gas sampling is made in a way in which a partial gas stream, still having the same temperature as the gas main stream, is branched off from the gas main stream and guided into the triboelectrical measuring chamber (5) immediately after it enters the sampling probe (2). Inside the triboelectrical measuring chamber (5), the measuring gas laden with dust particles and aerosols is cycloned, and the rubbing effect of these motion causes triboelectric signals to be generated.

The measuring gas stream is propelled by an injector (7) that is driven by a power air blower (9). A volume flow metering and/or monitoring device is integrated in the gas metering section so that constant conditions can be maintained for the partial gas stream, or computerized compensation is enabled as regards the impact the volume flow fluctuations may have on the triboelectric signal, respectively. Integrating a multi-way spherical valve (4) into the device enables cyclic backflushing of the triboelectrical measuring chamber (5) and the sampling probe (2 using power air supplied from the injector (7). The line through which the gas exits from the device is marked with position reference 8.

Figure 2:
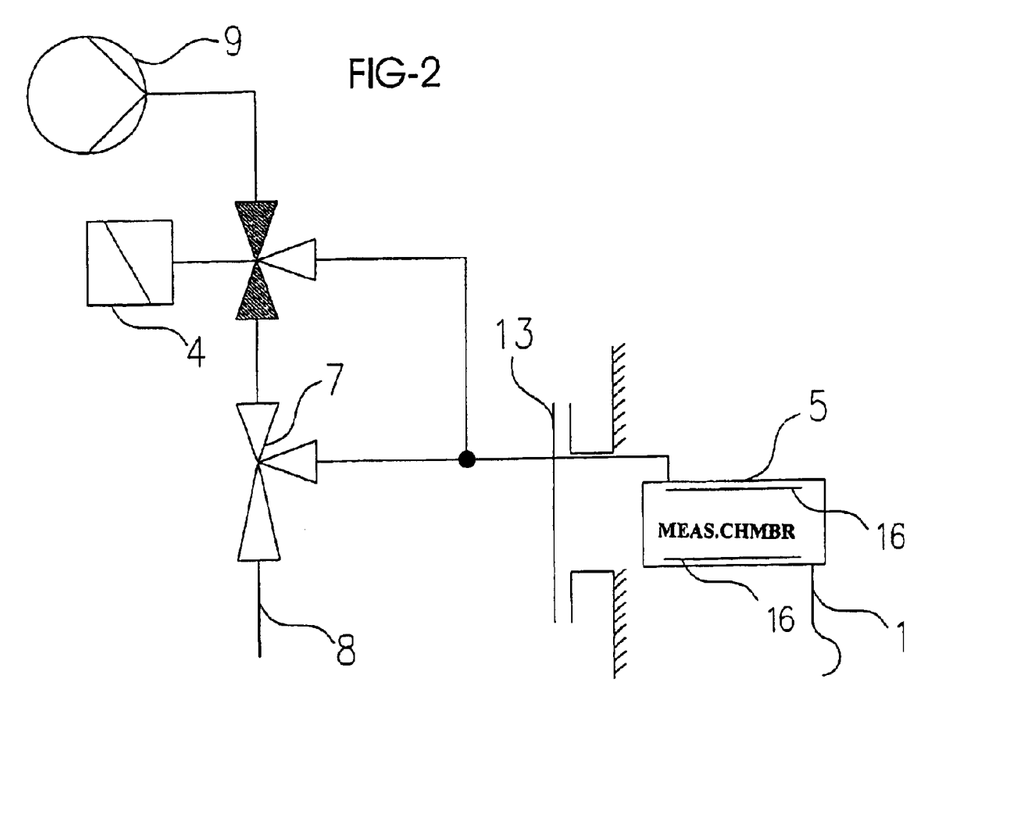

FIG. 2, in contrast to FIG. 1, shows a useful variation in which the triboelectrical measuring chamber (5) is arranged in the gas main stream. The hookshaped probe (1) is used for sampling, after which the sample, now being the partial gas stream, is fed into the triboelectrical measuring chamber (5).

Figure 3:
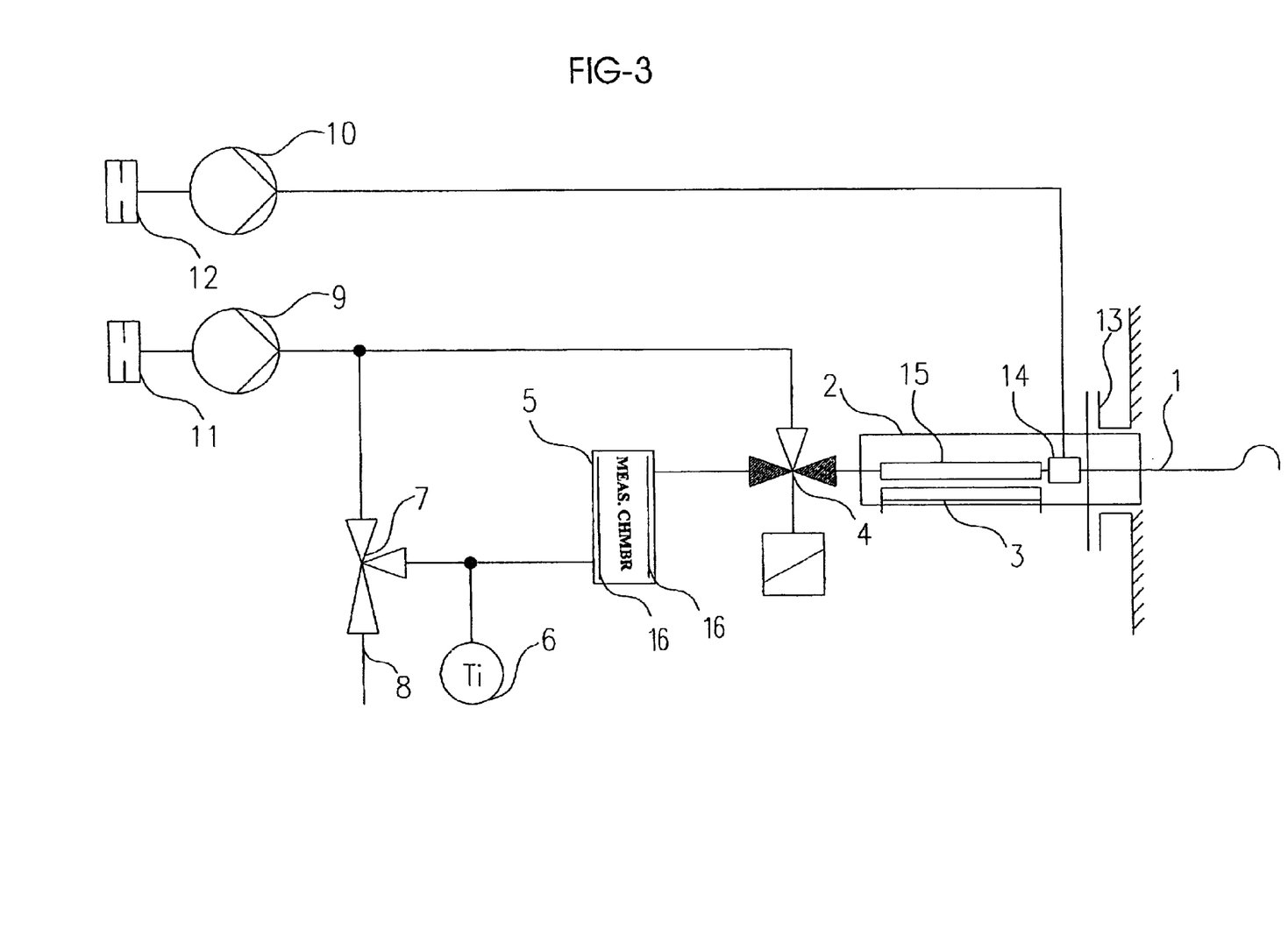
Figure 4:
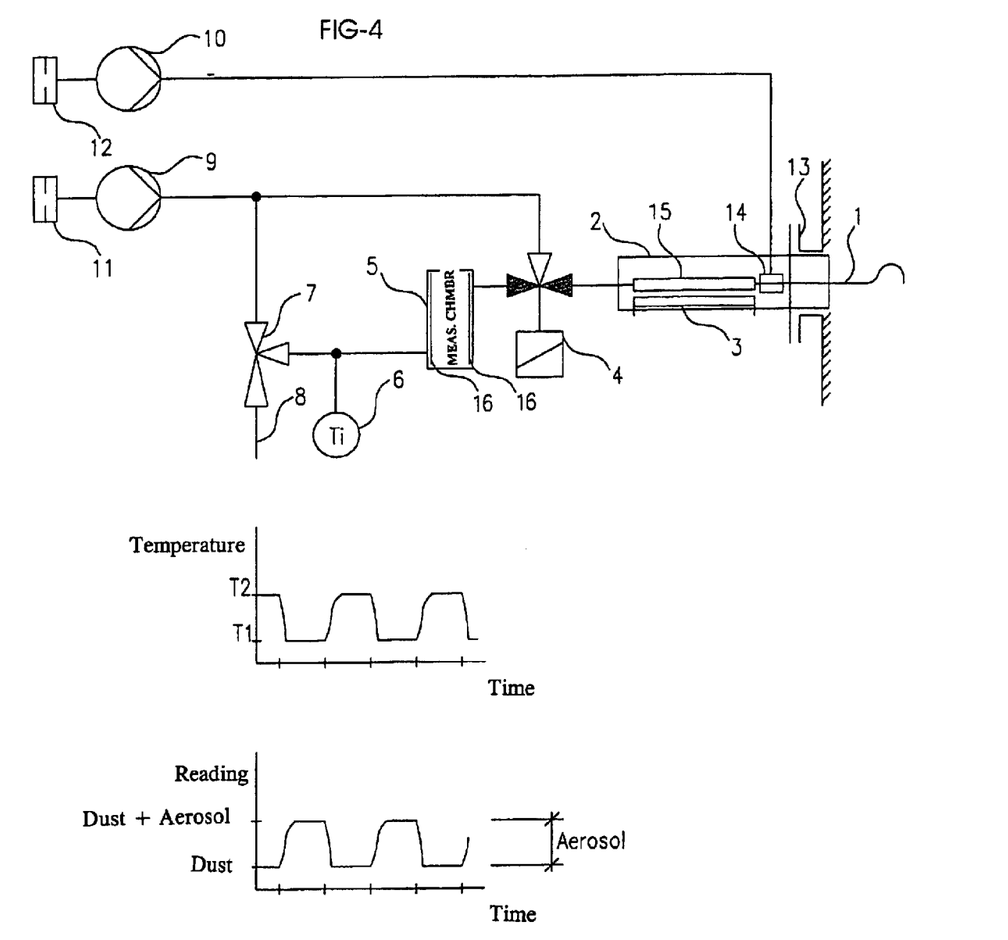

FIGS. 3 and 4 show how the triboelectric signals are generated when dust is contained in moist and tacky flue gases, that is to say we are talking about determination of aerosols in addition to dust measurements.

According to the invention, aerosol measuring is a differential measurement, in which all measurable particles and aerosols are measured and compared with the solid particles alone. If there is in place a flue gas matrix that contains volatile condensible components (organic compounds, water or acids), the components will exist in either gaseous or liquid/solid state, depending on the temperature. Gaseous components cannot be measured after the triboelectrical principle. It exists a temperature T2 at which the aerosols contained in the partial gas stream are completely evaporated. In this case, nothing else than dust is detected. At a second temperature T1, this temperature being lower than the first one, the volatile condensible components exist in form of aerosols in addition to the dust already in place. The difference found by comparing "dust plus aerosol" and "dust alone" is the desired "aerosol" value. Hence, the hardware configuration of the device as shown in FIGS. 1 and 2 needs to be supplemented.

After taking the flue gas sample by using the hook-shaped probe (1) and the probe for sampling measuring gas (2) as already described in greater detail, the branched-off partial gas stream is subjected to an intermittent temperature regime. This process is taking place in a specific chamber with intermittent temperature regime (15). In order to implement such intermittent temperature regime, use is made of a regulated probe heating device (3). Diluent air is supplied by a flushing air blower (10) with preceding suction filter (12).

The temperature regime applied during measuring the aerosol components as shown in FIG. 4 is maintained by employing a temperature measuring device (6).

Figure 5:
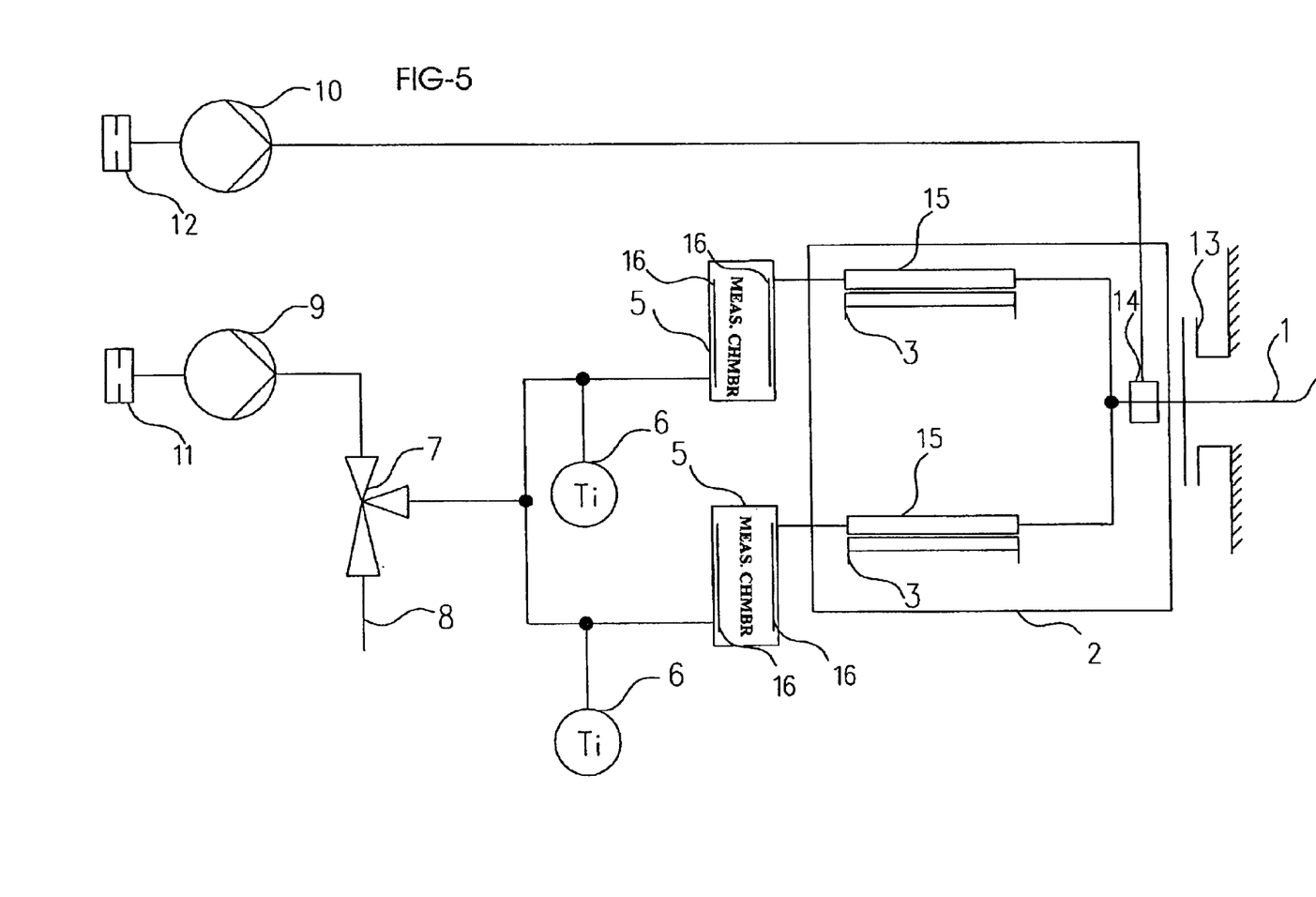

According to FIG. 5, aerosol measuring is made in two triboelectrical measuring chambers (5) working at two different temperature levels. In line with such layout, the partial stream taken by the hook-shaped probe (1) is divided into two branch streams each of them being heated up by a regulated probe heating device (3) specifically assigned to that branch in order to maintain a defined differential temperature. After exiting from the two triboelectrical measuring chambers (5), the differential temperatures Ta and Tb are determined by measuring devices (6).

Figure 6:
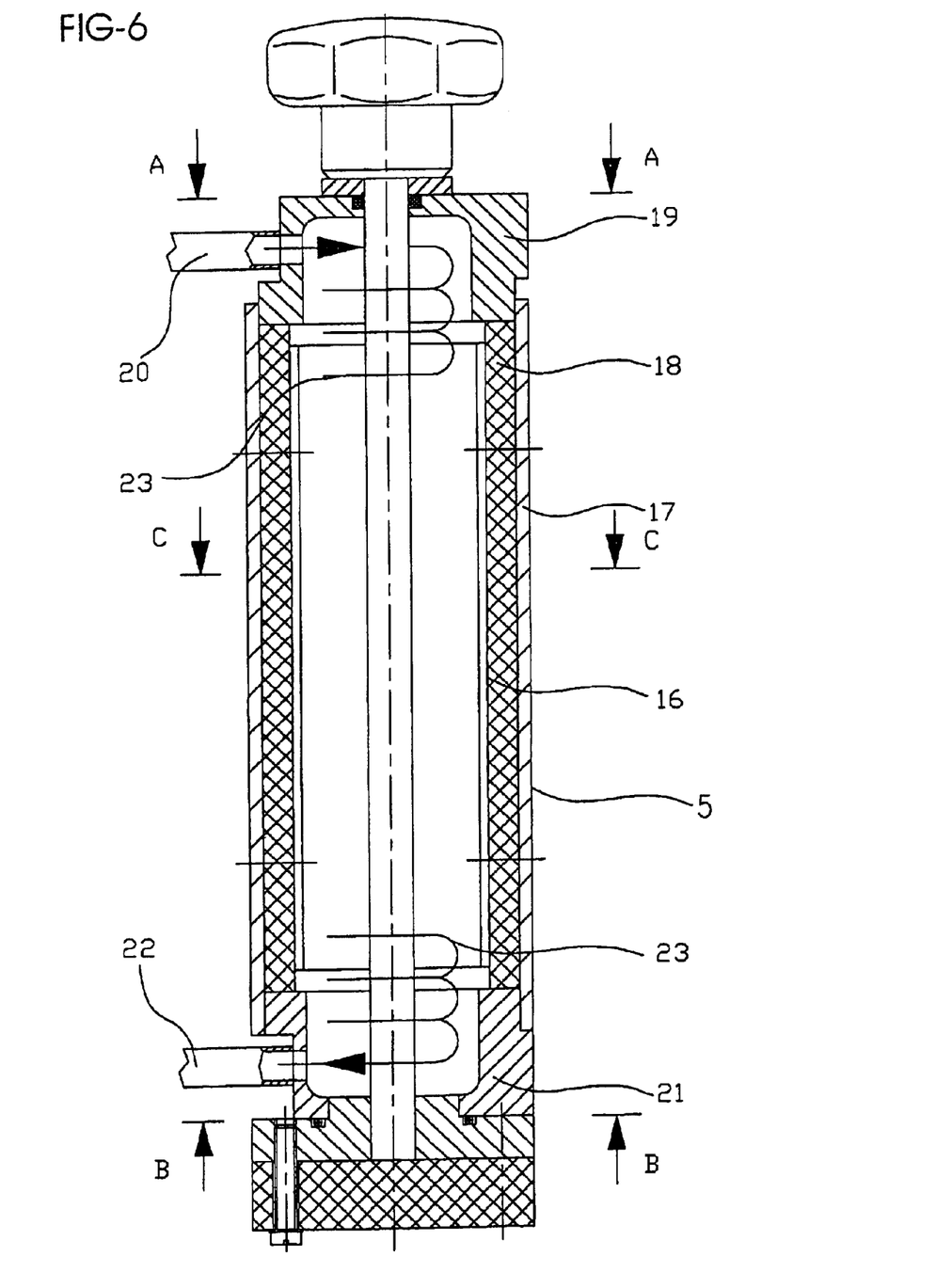

The subsequent FIGS. 6 through to 12 relate to suggestions in accordance with the invention, concerning the triboelectrical measuring chambers (5) as such or the design and layout of the sensors (16) inside the triboelectrical measuring chambers (5).

The triboelectrical measuring chamber (5) is now described in greater detail on the basis of a practical example with shell-like sensors (16).

Figure 8:
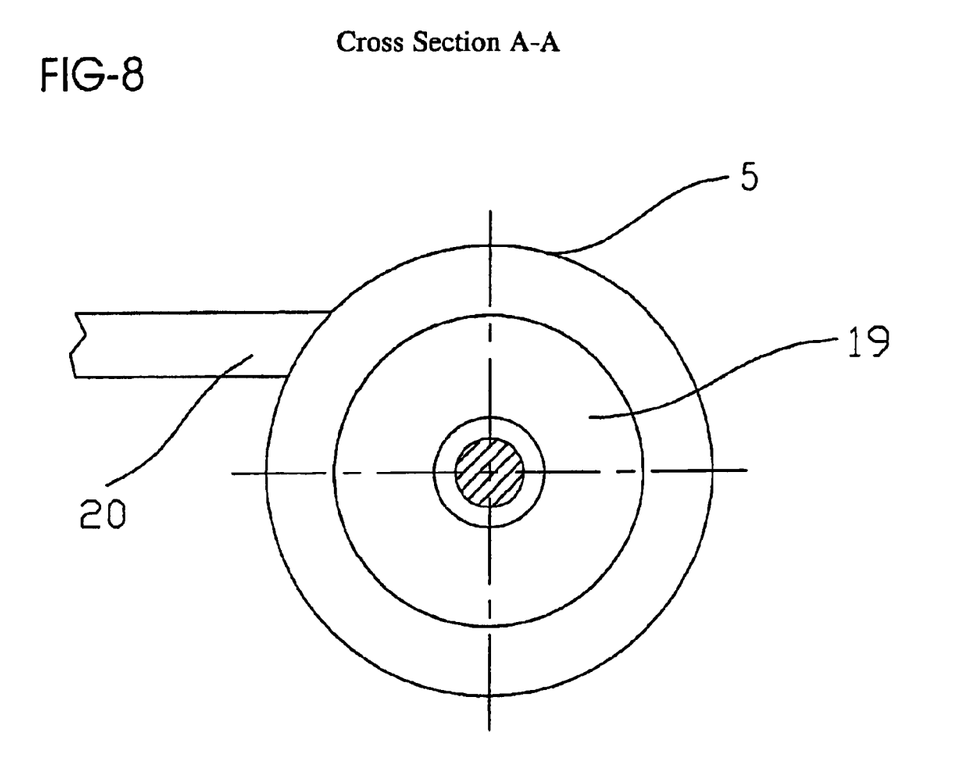
Figure 9:
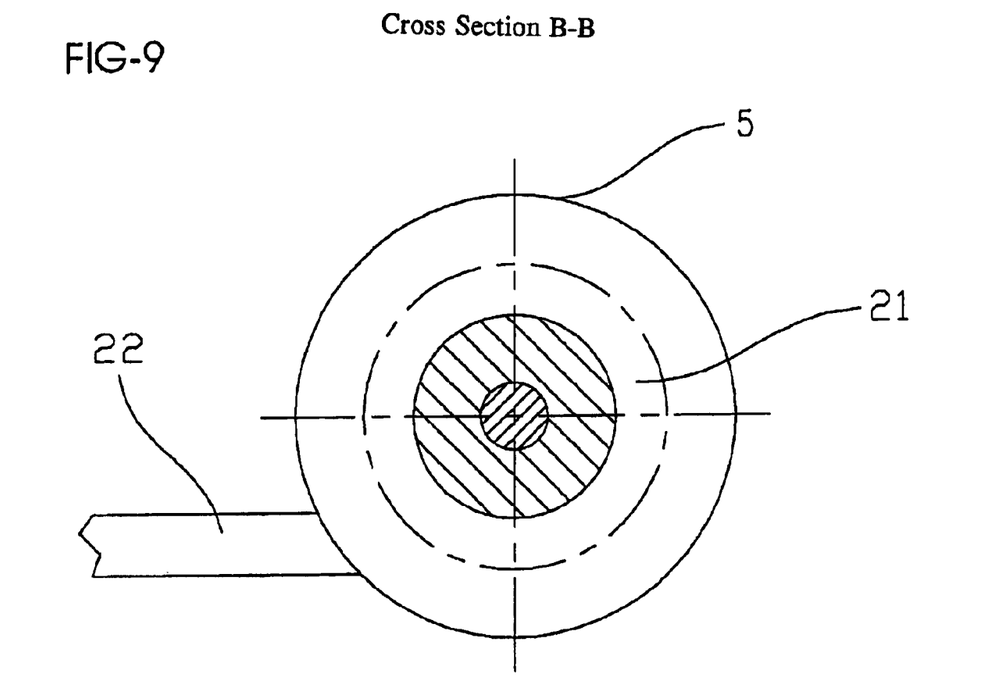
FIG. 9—Sectional view B—B, according to FIG. 6

According to FIG. 8, a dust/aerosol laden partial stream enters the intake cylinder (19) through the intake piece (20). The partial stream is discharged through an outlet cylinder (21) with tangentially arranged outlet pieces (22; please cf. FIG. 9).

Figure 7:
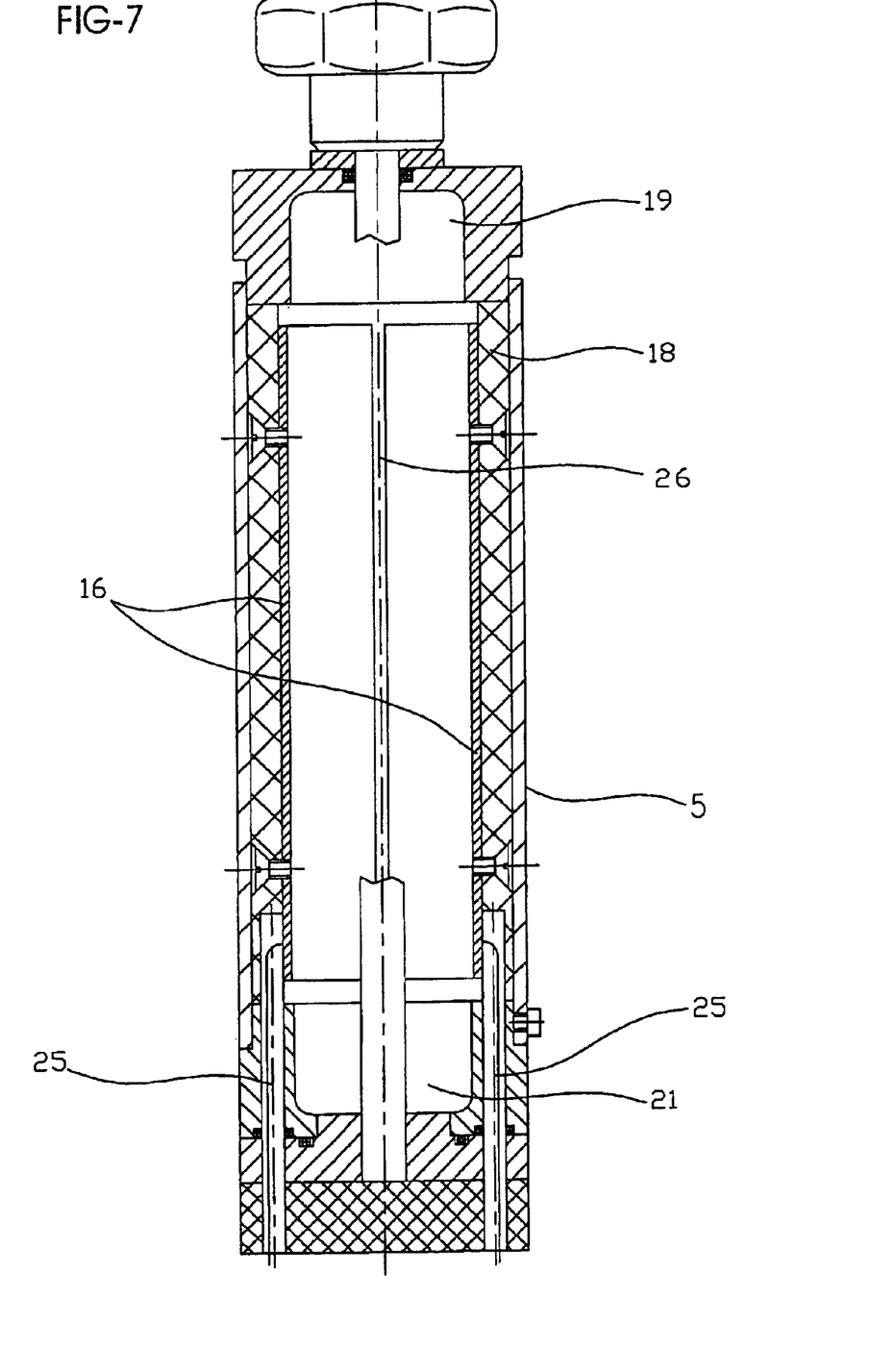

Electrically conductive, shell-like sensors (16) are arranged inside the tubeshaped triboelectrical measuring chamber (5). FIG. 7 shows the sensors' (16) shell-like structure. Electrical contact is prevented by the distance separation (26) in which the sensors (16) are located to each other. Other constructional measures prevent the sensors' (16) far ends from making electrical contact with the intake and outlet cylinders (19, 21). The sensors' (16) outward surfaces are wrapped in an insulating layer (18). This insulation layer prevents loss of heat and is nonconducting to electric current.

Both conditions are prerequisite for the proper functioning and working order of the measuring device. The measuring chamber's outer wall has a tubular design.

In contrast to FIG. 7, FIGS. 10, 11 and 12 demonstrate that sensors are not necessarily to be of a shell-like design. According to FIG. 10, several sensors (16) are arranged on the perimeter. From a bird's view, the latter are designed as ring segments.

Figure 10:
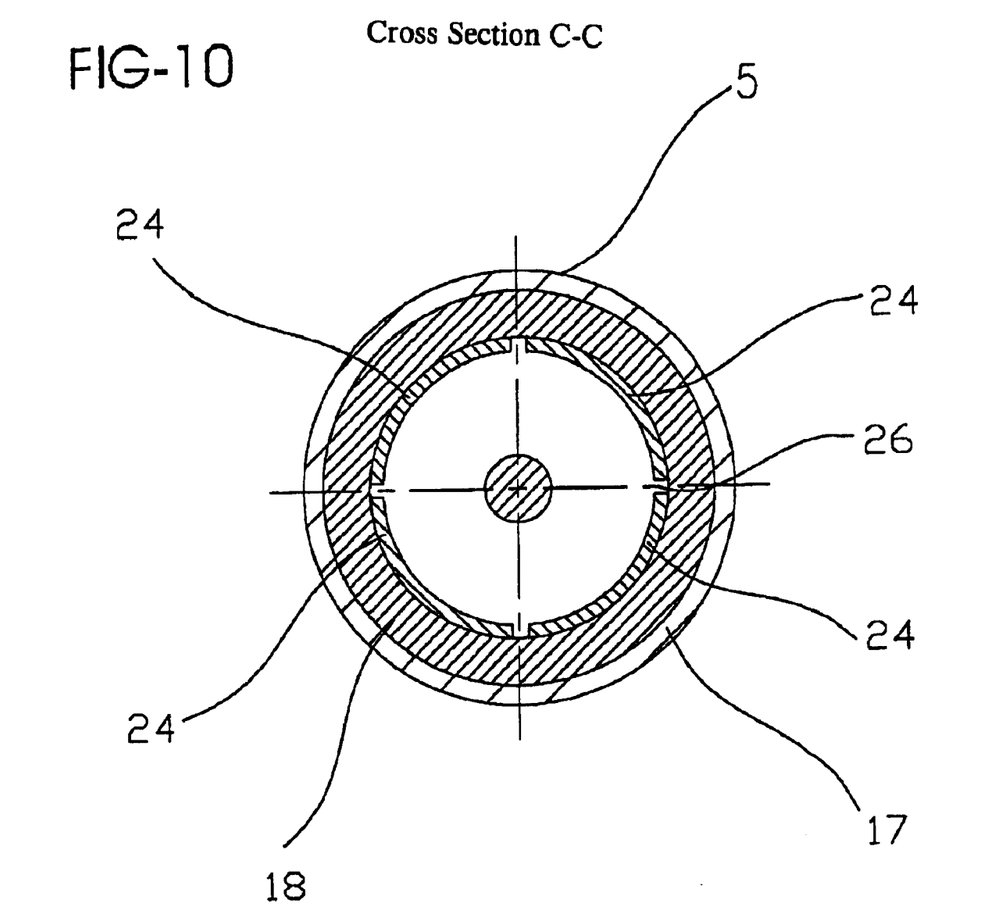
FIG. 10—Sectional view C—C, based on to FIG. 6 with four sensors being used

The ring segments' faces, being the sensors as such, are marked with position reference 24. To implement the measuring procedure, e.g. for nullification, these additional sensors may be very useful.

In addition, further reference should be made to the following variations of the sensors (16): As dust measuring relies on the charge exchanged between sensor and dust particles, sensors (16) may be of alternative design, such as hollow cylinder, round rod, trapezoidal section or square bar, with such sensors being arranged on the inward perimeter of the tubular triboelectrical measuring chamber (5) or in a central position. For details, reference is made to FIG. 11.

Figure 11:
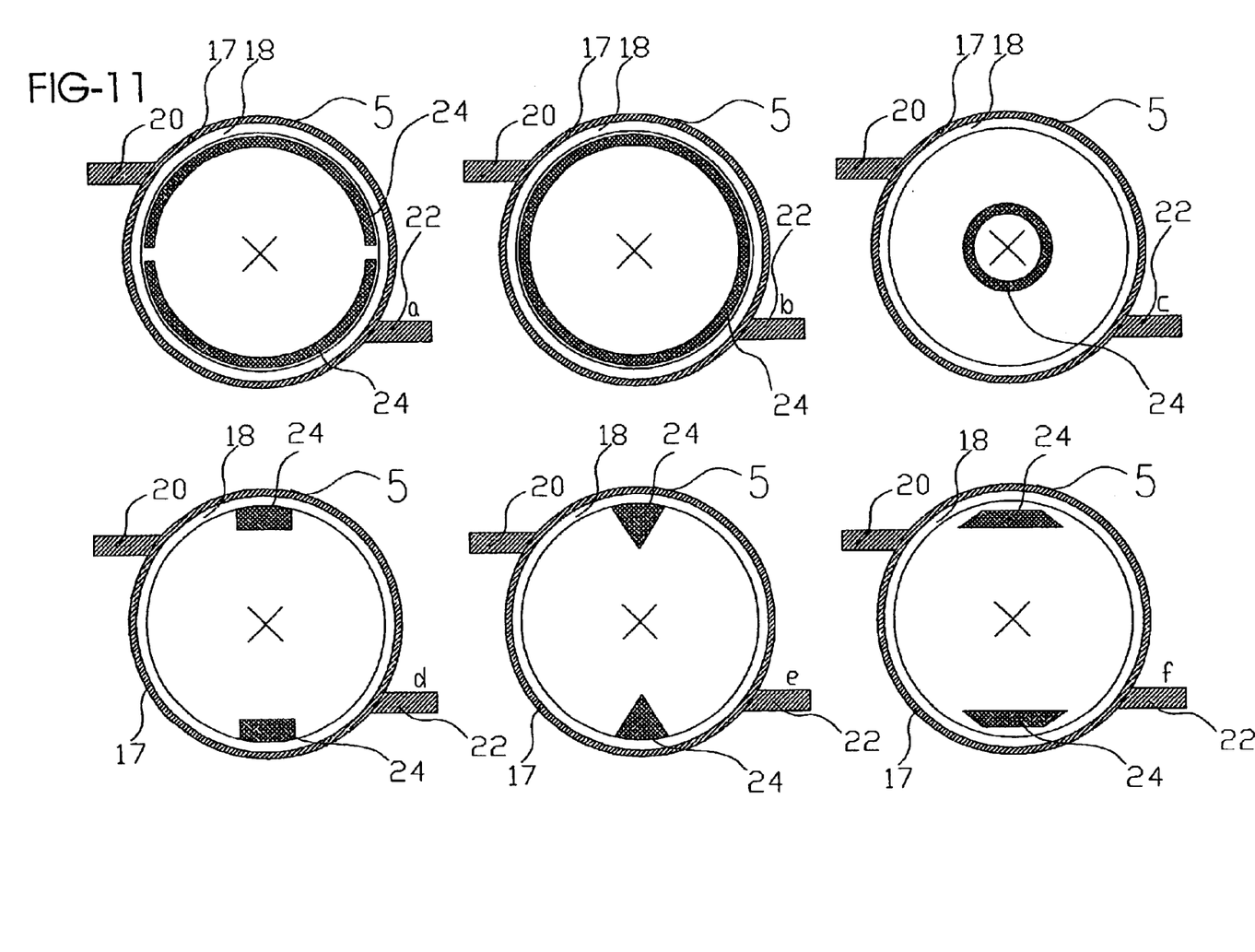
FIG. 11—Example of sensors in the triboelectrical measuring chamber, with tangential flow conditions FIG. 12—Example of sensors in the triboelectrical measuring chamber, with vertical and horizontal flow conditions

The sensors (16) may be either metallic conductive or provided with a specific coating, and they can be connected with equal or different potential.

The triboelectric signals must be read out and transmitted to further processing. Appropriate electric cabling is provided in the ducts (25).

The triboelectric effect occurs when the dust-laden gas stream (23) cyclones through the measuring chamber (15), with the dust particles rubbing across the sensors (16). The tangential admission direction of the gas stream (23) and its cyclone-like movement is basically the same as found in rotary separators. According to the invention, however, cycloning is used to implement a completely novel proposal, namely the amplification of the triboelectric effect for dust measurements. This will make possible measurements even at lower dust concentration levels.

Adjusting the signal level is also possible through the size and the design of the sensors selected.

Further advantageous impacts on the signal level may be achieved, for example, by coating the sensors with low-impedance PTFE.

The ring segments' faces, being the sensors as such, are marked with position reference 24. To implement the measuring procedure, e.g. for nullification, these additional sensors may be very useful.

In addition, further reference should be made to the following variations of the sensors (16):

As dust measuring relies on the charge exchanged between sensor and dust particles, sensors (16) may be of alternative design, such as hollow cylinder, round rod, trapezoidal section or square bar, with such sensors being arranged on the inward perimeter of the tubular triboelectrical measuring chamber (5) or in a central position. For details, reference is made to FIG. 11.

The sensors (16) may be either metallic conductive or provided with a specific coating, and they can be connected with equal or different potential.

The triboelectric signals must be read out and transmitted to further processing. Appropriate electric cabling is provided in the ducts (25).

The triboelectric effect occurs when the dust-laden gas stream (23) cyclones through the measuring chamber (15), with the dust particles rubbing across the sensors (16). The tangential admission direction of the gas stream (23) and its cyclone-like movement is basically the same as found in rotary separators. According to the invention, however, cycloning is used to implement a completely novel proposal, namely the amplification of the triboelectric effect for dust measurements. This will make possible measurements even at lower dust concentration levels.

Adjusting the signal level is also possible through the size and the design of the sensors selected.

Further advantageous impacts on the signal level may be achieved, for example, by coating the sensors with low-impedance PTFE.

Figure 12:
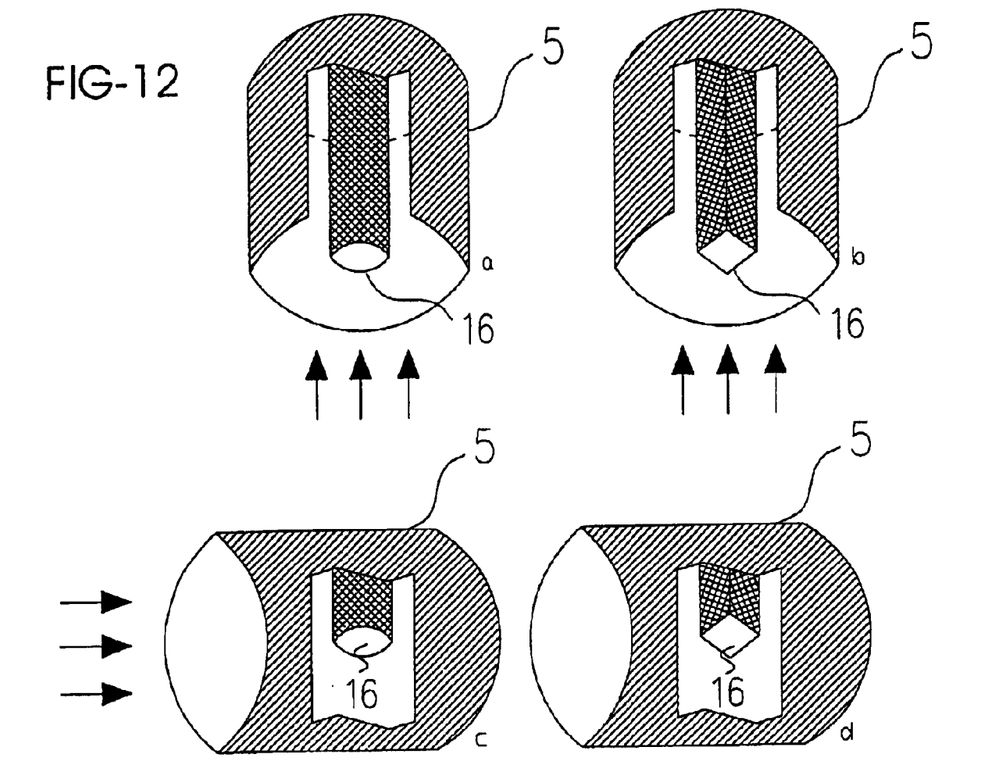

Finally, reference should be made to further variations of the sensors and how they are arranged inside the measuring chamber. As can be seen from FIG. 12, sensors may be located also in a central position so that, besides tangential flow conditions, even centrical flow conditions can be realized after the speed has been increased in advance, FIG. 12 depicts examples of vertical and horizontal layouts of the triboelectrical measuring chamber.

A redundant sensor layout enables hardware self-checks as to the uniform generation of the triboelectric signals. This may have a positive influence, for example on the quality of measurements.

What is claimed is:

1. A method for the extractive triboelectric measurement of dust and aerosols in streaming gases, comprising:
   branching off a partial gas stream from a dust-laden main gas stream;
   directing said partial gas stream through an intake cylinder into a tube-shaped triboelectrical measuring chamber equipped with sensors;
   moving the partial gas stream across the sensors, thereby causing the dust and aerosol particles contained in the latter to be rubbed against said sensors whereby an electrical charge exchange is generated;
   directing the partial gas stream through an outlet exit from the triboelectrical measuring chamber; and
   before the partial gas stream enters the triboelectrical measuring chamber, evaporating a full range of aerosols by increasing the temperature of the partial gas stream in such a way that nothing other than dust particles are detected, and decreasing the temperature of the partial gas stream to a level at which no aerosols are evaporated any more, and ascertaining the aerosol concentration from a difference between signals read out for "dust alone" and for "aerosols plus dust".

2. Method according to claim 1, wherein velocity and temperature of the gas stream flowing through the triboelectrical measuring chamber is varied.

3. Method according to claim 1 or 2, further comprising reading out a change from the sensors.

4. Method according to claim 1 or 2, wherein the entry of the partial gas stream into the triboelectrical measuring chamber from the intake cylinder is tangential, after which said rubbing is effected by a cyclone-like motion of said partial gas stream across the sensors.

5. Method according to claim 1 or 2, further comprising implementing an intermittent temperature regime for determining the aerosol concentration.

6. Method according to claim 1, comprising right after the partial gas steam is branched-off from the gas main stream, performing an effective dilution with a diluent air stream by using a proportioning nozzle, after which the resultant mixture, having now a definite temperature, flows into the triboelectrical measuring chamber.

7. An apparatus for extractive triboelectric measurement of dust and aerosols in steaming gases, that results from electrical charge exchange generation comprising:

a tubular triboelectrical measuring chamber contains sensors;

an insulation layer between an outer wall of the measuring chamber and the sensors, the insulating layer completely surrounding the sensors;

an intake cylinder;

an upper end of the measuring chamber having an intake piece connected to intake cylinder;

an outlet cylinder;

a lower end of the measuring chamber having an outlet piece that is connected to the outlet cylinder, the outlet cylinder and the intake cylinder having no electric contact to the sensors; and the sensors being coated with low-impedance PTFE.

8. Apparatus according to claim 7, wherein the sensors are shell-shaped.

9. Apparatus according to claim 7, wherein connection of the intake piece to the intake cylinder is in tangential direction to the intake cylinder.

10. Apparatus according to claim 7, wherein the triboelectrical measuring chamber is arranged either inside or outside a cross-sectional area of the gas main stream.

11. An apparatus for extractive triboelecric measurement of dust and aerosols in streaming gases, that results from electrical charge exchange generation comprising:

a tubular triboelectrical meting chamber containing sensors;

an insulation layer between an outer wall of the measuring chamber and the sensors, the insulating layer completely surrounding the sensors;

an intake cylinder;

an upper end of the measuring chamber having an intake piece connected to intake cylinder, an outlet cylinder;

a lower end of the measuring chamber having an outlet piece that is connected to the outlet cylinder, the outlet cylinder and the intake cylinder having no electric contact to the sensors; and the sensors numbering more than two and in plan view constituting a set of segments of a circular ring where the are spaced at such distances as to prevent any electric contact therebetween.

12. Apparatus according to claim 11, wherein the sensors are shell-shaped.

13. Apparatus according to claim 11, wherein connection of the intake piece to the intake cylinder is in tangential direction to the intake cylinder.

14. Apparatus according to claim 11, wherein the triboelectrical measuring chamber is arranged either inside or outside a cross-sectional area of the gas main stream.

15. An apparatus for extractive triboelectric measurement of dust and aerosols in streaming gases, that results from electrical charge exchange generation comprising:

a tubular triboelectrical measuring chamber containing sensors;

an insulation layer between an outer wall of the measuring chamber and the sensors, the insulating layer completely surrounding the sensors;

an intake cylinder;

an upper end of the measuring chamber having an intake piece connected to intake cylinder;

an outlet cylinder;

a lower end of the measuring chamber having an outlet piece that is connected to the outlet cylinder, the outlet cylinder and the intake cylinder having no electric contact to the sensors; and the sensors being of different geometrical patterns adapted for vertical and horizontal flow conditions.

16. Apparatus according to claim 15, wherein the sensors are shell-shaped.

17. Apparatus according to claim 15, wherein connection of the intake piece to the intake cylinder is in tangential direction to the intake cylinder.

18. Apparatus according to claim 15, wherein the triboelectrical measuring chamber is arranged either inside or outside a cross-sectional area of the gas main stream.

19. An apparatus for extractive triboelectric measurement of dust and aerosols in streaming gases, that results from electrical charge exchange generation comprising:

a tubular triboelectrical measuring chamber containing sensors;

an insulation layer between an outer wall of the measuring chamber and the sensors, the insulating layer completely surrounding the sensors;

an intake cylinder;

an upper end of the measuring chamber having an intake piece connected to intake cylinder;

an outlet cylinder;

a lower end of the measuring chamber having an outlet piece that is connected to the outlet cylinder, the outlet cylinder and the intake cylinder having no electric contact to the sensors; and a regulated probe heating device arranged around the measuring chamber that is regulated to operate with an intermittent temperature regime, a probe for sampling measuring gas, a proportioning nozzle for providing a supply of diluent air situated inside the probe, a multi-way spherical valve for implementing back-flush operation by using a power air blower arranged between the probe and the triboelectrical measuring chamber, and an injector located downstream from the triboelectrical measuring chamber during operation of said injector in such a way that the partial gas stream is drawn through the measuring chamber.

20. Apparatus according to claim 19, wherein the sensors are shell-shaped.

21. Apparatus according to claim 19, wherein connection of the intake piece to the intake cylinder is in tangential direction to the intake cylinder.

22. Apparatus according to claim 19, wherein the triboelectrical measuring chamber is arranged either inside or outside a cross-sectional area of the gas main stream.

23. A method for extractive triboelectric measurement of dust and aerosols in a gas stream, comprising:

setting a temperature of at least a portion of the gas stream to a first temperature at which a full range of aerosols is evaporated in such a way that nothing other than dust particles are detectable by triboelectric measurement;

applying the at least a portion of the gas stream set at the first temperature to a triboelectrical measuring apparatus such that dust particles contained in the gas stream produce a first triboelectric signal;

measuring the first triboelectric signal;

setting a temperature of at least a portion of the gas stream to a second temperature at which a full range of aerosols are not evaporated in such that both dust and aerosol particles are detectable by triboelectric measurement;

applying the at least a portion of the gas stream set at the second temperature to a triboelectrical measuring apparatus such that dust and aerosol particles contained in the gas stream produce a second triboelectric signal;

measuring the second triboelecric signal; and ascertaining an aerosol concentration from a difference between the first triboelectric signal and the second triboelectric signal.

24. The method of claim 23 wherein the triboelectric measuring apparatus is a single triboelectric chamber and the first triboelectric signal and the second triboelectric signal are generated sequentially by applying the at least a portion of the gas stream to the single triboelectrical measuring chamber and alternatingly setting the temperature of the at least a portion of the gas stream to the first temperature and the second temperature.

25. The method of claim 23 wherein the triboelectric measuring apparatus includes a first triboelectric chamber and a second triboelectric chamber and the first triboelectric signal and the second triboelectric signal are generated concurrently by dividing the at least a portion of the gas stream and respectively applying first and second divided portions to the first triboelectrical measuring chamber and the second triboelectrical measuring chamber while setting the temperature of the first divided portion of the at least a portion of the gas stream applied to the first triboelectric measuring chamber to the first temperature to generate the first triboelectric signal and setting the temperature of the second divided portion of the at least a portion of the gas stream applied to the second triboelectric measuring chamber to the second temperature to generate the second triboelectric signal.

26. An apparatus for extractive triboelectric measurement of dust and aerosols in a gas stream, comprising:

a temperature control device for setting a temperature of at least a portion of the gas stream to a first temperature at which a full range of aerosols is evaporated in such a way that nothing other than dust particles are detectable by triboelectric measurement, and for setting a temperature of at least a portion of the gas stream to a second temperature at which a full range of aerosols are not evaporated in such that both dust and aerosol particles are detectable by triboelectric measurement;

a triboelectric measuring apparatus accepting the at least a portion of the gas stream set at the first temperature to produce a first triboelectric signal and accepting the at least a portion of the gas stream set at the second temperature to produce a second triboelectric signal; and a comparing device ascertaining an aerosol concentration from a difference between the first triboelectric signal and the second triboelectric signal.

* * * * *